United States Patent
Zhang et al.

(10) Patent No.: US 12,384,795 B2
(45) Date of Patent: *Aug. 12, 2025

(54) PYRIMIDO[5,4-B]PYRROLIZIN COMPOUND, OPTICAL ISOMER THEREOF, PREPARATION METHOD THEREFOR AND USE THEREOF

(71) Applicant: SHANGHAI INSTITUTE OF MATERIA MEDICA, CHINESE ACADEMY OF SCIENCES, Shanghai (CN)

(72) Inventors: Ao Zhang, Shanghai (CN); Jian Ding, Shanghai (CN); Hua Xie, Shanghai (CN); Zilan Song, Shanghai (CN); Yu Xue, Shanghai (CN); Li Xing, Shanghai (CN); Linjiang Tong, Shanghai (CN); Meiyu Geng, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 891 days.

This patent is subject to a terminal disclaimer.

(21) Appl. No.: 17/606,121

(22) PCT Filed: Apr. 24, 2020

(86) PCT No.: PCT/CN2020/086787
§ 371 (c)(1),
(2) Date: Oct. 25, 2021

(87) PCT Pub. No.: WO2020/216343
PCT Pub. Date: Oct. 29, 2020

(65) Prior Publication Data
US 2022/0204518 A1   Jun. 30, 2022

(30) Foreign Application Priority Data

Apr. 24, 2019 (CN) .......................... 201910334619.9

(51) Int. Cl.
*C07D 487/14* (2006.01)
*A61P 35/00* (2006.01)

(52) U.S. Cl.
CPC ............ *C07D 487/14* (2013.01); *A61P 35/00* (2018.01)

(58) Field of Classification Search
CPC ................................................... C07D 487/14
See application file for complete search history.

(56) References Cited

U.S. PATENT DOCUMENTS 10,829,491 B2 * 11/2020 Zhang ..................... A61P 37/02

FOREIGN PATENT DOCUMENTS

CN    101175755 A    5/2008
CN    108101905 A    6/2018

OTHER PUBLICATIONS

Yu Xue et al., "Discovery of 4, 7-Diamino-5(4-phenoxyphenyl)-6-methyle-ne-pyrimino[5, 4-b]pyrrolizines as Novel Bruton's Tyrosine Kinase Inhibitors", Journal of Medicinal Chemistry, May 1, 2018.

* cited by examiner

*Primary Examiner* — Golam M Shameem
(74) *Attorney, Agent, or Firm* — NKL Law; Bin Lu; Allen Xue

(57) ABSTRACT

The present invention relates to a pyrimido[5,4-b]pyrrolizin compound represented by general formula I, an optical isomer thereof, a preparation method therefor, a pharmaceutical composition containing same, and a use thereof. The compound according to the present invention has good inhibitory activity on the kinase BTK at both the molecular level and the cellular level. Meanwhile, the compound also has good anti-tumor activity and pharmacokinetic properties in vivo.

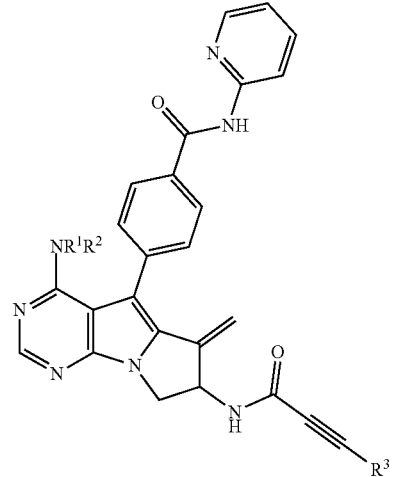

14 Claims, 1 Drawing Sheet

PYRIMIDO[5,4-B]PYRROLIZIN COMPOUND, OPTICAL ISOMER THEREOF, PREPARATION METHOD THEREFOR AND USE THEREOF

TECHNICAL FIELD

The present invention relates to a pyrimido[5,4-b]pyrrolizin compound, optical isomers, preparation methods, pharmaceutical compositions and uses thereof, and in particular to a pyrimido[5,4-b]pyrrolizin compound used as a small molecule inhibitor targeting BTK kinase, preparation method, pharmaceutical composition thereof and use of which in the preparation of a medicament for treating diseases related to BTK kinase signal transduction pathway.

BACKGROUND ART

Bruton's tyrosine kinase (BTK) is a non-receptor tyrosine kinase belonging to TEC tyrosine kinase family. TEC family members include Tec, Bmx, BTK, Itk and Txk. BTK is the most widely studied member of TEC family and is a key regulator in B cell receptor (BCR) signal pathway. BTK is widely expressed in many types of malignant hematological tumors and participates in the proliferation, differentiation and apoptosis of B cells. Therefore, BTK has become an important molecular target for drug therapy of malignant hematological tumors.

Ibrutinib, a small molecule inhibitor targeting BTK kinase developed by Pharmacyclics, an international pharmaceutical company, was approved by FDA in November 2013 as a breakthrough therapeutic drug for clinical treatment of relapsed or refractory mantle cell lymphoma (MCL). However, Ibrutinib also has a good inhibitory effect on Tec and EGFR kinases, which leads to great toxic and side effects. Acalabrutinib (ACP-96), the second generation BTK inhibitor listed in 2017, has high selectivity for BTK and lacks irreversible activity for off-target kinase. In Phase I/II clinical trials of patients with relapsed/refractory chronic lymphocytic leukemia (CLL), the total response rate is high. Zanubrutinib (BGB-3111), another highly selective irreversible inhibitor of BTK in BeiGene in China, recently released positive clinical data, especially in the indications of mantle cell lymphoma (MCL), and granted Breakthrough Therapy Designation (BTD) by FDA on Jan. 14, 2019. Generally speaking, the first generation inhibitors have high inhibitory activity on BTK, but poor target selection and bioavailability; the second generation inhibitors have good selectivity, but the inhibition rate of BTK is lower than that of the first generation inhibitors. Structurally, the core skeletons of compounds on the market or under research are all bicyclic systems.

In order to obtain a new generation of BTK inhibitors with high activity of the first generation inhibitors and good selectivity of the second generation inhibitors, Shanghai Institute of Materia Medica, Chinese Academy of Sciences disclosed a class of tricyclic compounds with unique structure in patent CN108101905A. Among them, pyrimido[5,4-b]indazine compounds S1 and S10 and pyrimido[5,4-b]pyrrolizin compounds S18, S19 and S20 showed high BTK inhibitory activity. In the further work, S-configuration compounds of S18, S19 and S20 (i.e. S18s, S19s and S20s) were synthesized. However, further study found that S1, S10, S18s and S19s were unstable in metabolism, and the 4-position of terminal phenyl was easy to be oxidized. Meanwhile, the oral bioavailability of compound S20s was not ideal.

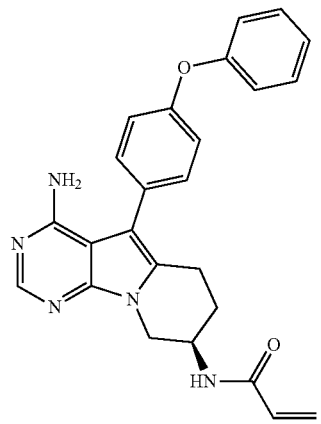

S1

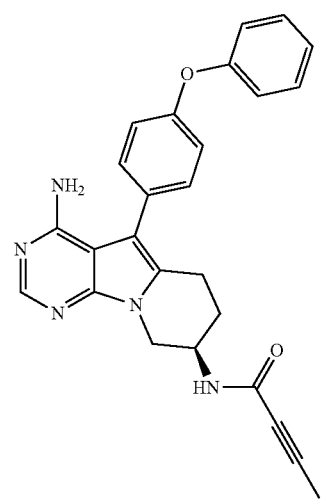

S10

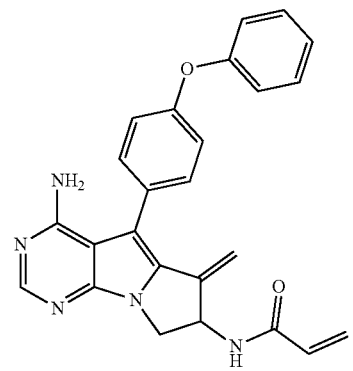

S18s

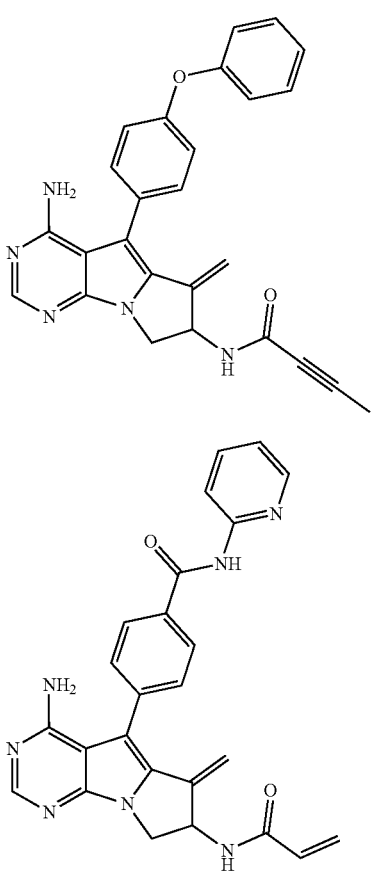

TECHNICAL PROBLEMS

The present invention aims to solve one of the following technical problems: To provide a compound that has excellent BTK inhibitory activity and maintains good BTK inhibitory selectivity compared with known compounds.

To provide a compound as a small molecule inhibitor targeting BTK kinase having excellent BTK inhibitory activity, better BTK inhibitory selectivity and better oral administration performance compared with known compounds.

To provide a compound as a small molecule inhibitor targeting BTK kinase having excellent BTK inhibitory activity, better BTK inhibitory selectivity and better metabolic stability compared with known compounds.

To provide a compound as a small molecule inhibitor targeting BTK kinase having better oral administration performance and better metabolic stability compared with known compounds.

To provide a compound as a small molecule inhibitor targeting BTK kinase having excellent BTK inhibition activity, better BTK inhibition selectivity, better oral administration performance and better metabolic stability compared with known compounds.

To provide a compound as a small molecule inhibitor targeting BTK kinase having better in vivo anti-tumor activity compared with known compounds.

SUMMARY OF THE INVENTION

In view of the above problems, after further study, the applicant found a pyrimido[5,4-b]pyrrolizin compound, especially compound S17016, which not only has excellent in vivo and in vitro activity, but also has good oral administration performance and metabolic stability. It is obviously superior to the marketed drug ibrutinib and other control compounds, and has the potential to treat diseases related to BTK kinase signal transduction pathway. On above basis, the present invention has been completed.

It is an object of the present invention to provide a pyrimido[5,4-b]pyrrolizin compound.

It is another object of the present invention to provide pharmaceutically acceptable salts, enantiomers, diastereomers, optical isomers, racemates, deuterated derivatives, solvates or hydrates of the compound.

It is an object of the present invention to provide a preparation method of the compound.

It is another object of the present invention to provide a pharmaceutical composition comprising the compound, pharmaceutically acceptable salts, enantiomers, diastereomers, optical isomers, racemates, deuterated derivatives, solvates or hydrates thereof.

It is another object of the present invention to provide a use of the compound, pharmaceutically acceptable salts, enantiomers, diastereomers, optical isomers, racemates, deuterated derivatives, solvates or hydrates thereof in the preparation of a medicament for the treatment of diseases associated with the BTK kinase signal transduction pathway.

It is another object of the present invention to provide a use of the compound, pharmaceutically acceptable salts, enantiomers, diastereomers, optical isomers, racemates, deuterated derivatives, solvates or hydrates thereof in the preparation of a medicament for the treatment, prevention or regulation of cancer.

According to one aspect of the present invention, it provides a pyrimido[5,4-b]pyrrolizin compound represented by general formula I, pharmaceutically acceptable salts, enantiomers, diastereomers, optical isomers, racemates, deuterated derivatives, solvates or hydrates thereof:

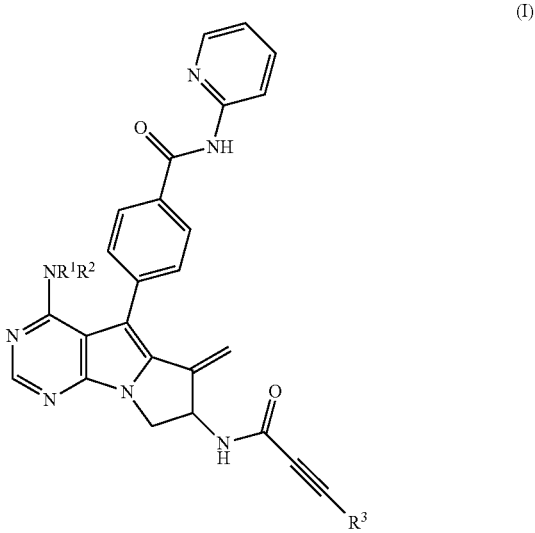

(I)

wherein $R^1$ and $R^2$ are each independently H or $C_1$-$C_{10}$ alkyl, preferably H or $C_1$-$C_6$ alkyl, more preferably H or $C_1$-$C_3$ alkyl, more preferably H;

$R^3$ is H or $C_1$-$C_{10}$ alkyl, preferably H or $C_1$-$C_6$ alkyl, more preferably H or $C_1$-$C_3$ alkyl, more preferably methyl.

Preferably, the compound of Formula I is a compound represented by formula I-1:

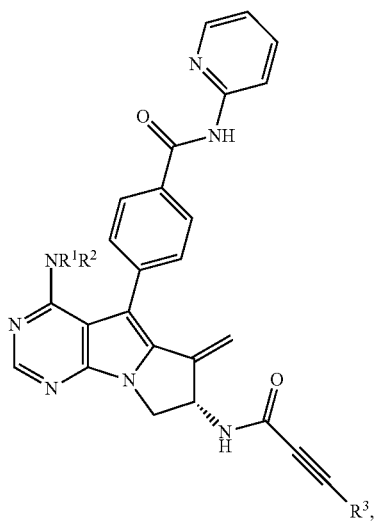

wherein $R^1$, $R^2$ and $R^3$ are as defined above.

Preferably, the compound of formula I is

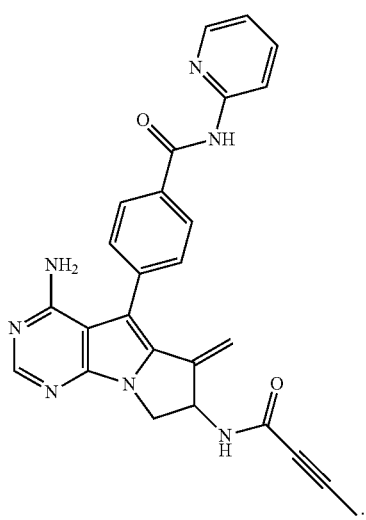 [SMILES: C=C1c2c(-c3ccc(C(=O)Nc4ccccn4)cc3)c3c(N)ncnc3n2CC1NC(=O)C#CC]

Preferably, the compound of formula I-1 is

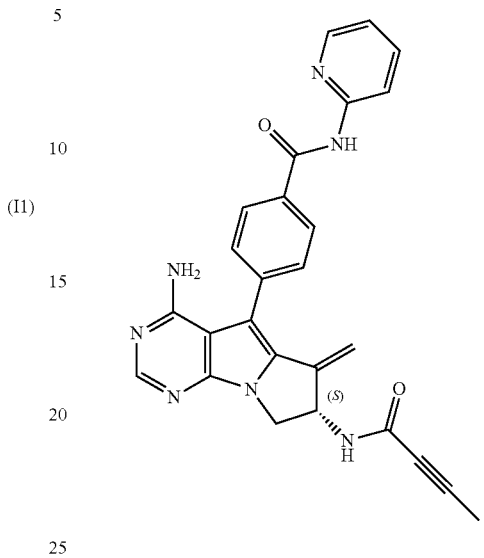

The compound of the present invention may have asymmetric centers, chiral axes and chiral planes and may be present in the form of enantiomers, diastereomers, optical isomers, racemates and mixtures thereof. For example, when chiral carbon atoms are present in the structure of the compound, each chiral carbon atom may optionally be of R configuration or S configuration, or a mixture of R configuration and S configuration.

Pharmaceutically acceptable salts of the compound may be conventional non-toxic salts formed by the reaction of the compound with an inorganic or organic acid. For example, conventional non-toxic salts can be prepared by reacting a compound with an inorganic acid or organic acid. The inorganic acid includes hydrochloric acid, hydrobromic acid, sulfuric acid, nitric acid, sulfamic acid, phosphoric acid, etc., and the organic acid includes lysine, arginine, ornithine, citric acid, tartaric acid, lactic acid, pyruvic acid, acetic acid, benzenesulfonic acid, p-toluenesulfonic acid, methanesulfonic acid, naphthalenesulfonic acid, ethanesulfonic acid, naphthalenedisulfonic acid, maleic acid, malic acid, malonic acid, fumaric acid, succinic acid, propionic acid, oxalic acid, trifluoroacetic acid, stearic acid, pamoic acid, hydroxymaleic acid, phenylacetic acid, benzoic acid, salicylic acid, glutamic acid, ascorbic acid, p-aminobenzenesulfonic acid, 2-acetoxybenzoic acid, aspartic acid and isethionic acid, etc.

The deuterated derivative of the compound of the present invention, i.e. the deuterated form of the compound of the general formula I or I-1 compound, can contain the derivative in which any one or several hydrogen atoms in the structure of the compound of the general formula I or I-1 are replaced by the isotope deuterium atom.

According to one aspect of the present invention, it provides a method for preparing the above-mentioned pyrimido[5,4-b]pyrrolizin compound, the method comprises the following steps:

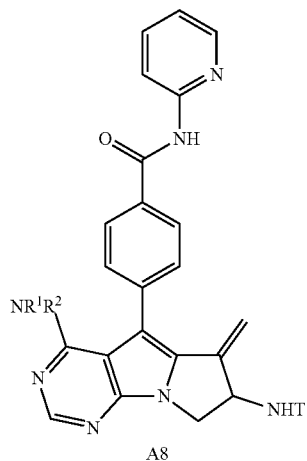 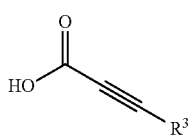

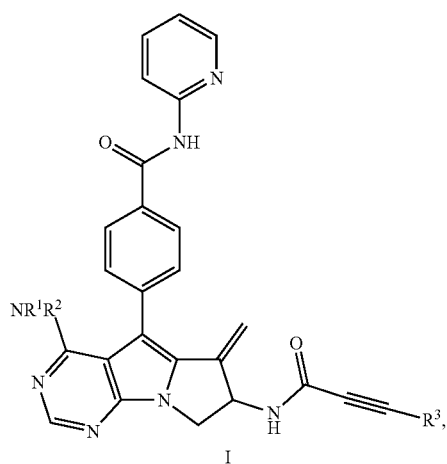

wherein $R^1$, $R^2$ and $R^3$ are as defined above;

preferably

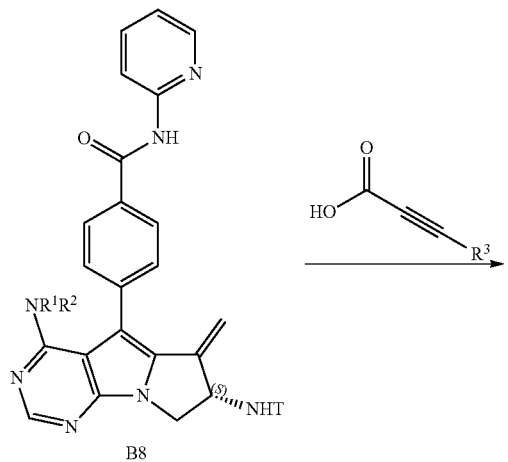

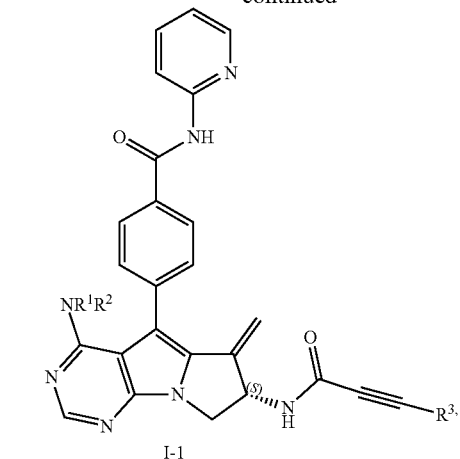

wherein $R^1$, $R^2$ and $R^3$ are as defined above;

removing the protective group T from reactant A8 or B8, and then reacting with

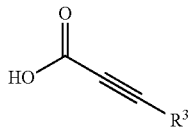

to obtain the compound of the general formula I or the compound of the general formula I-1, wherein the protective group T comprises tert-butoxycarbonyl, benzyloxycarbonyl, fluorenylmethyloxycarbonyl, allyloxycarbonyl, trimethylsilylethoxycarbonyl, methoxycarbonyl, ethoxycarbonyl, phthalimido, p-toluenesulfonyl, trifluoroacetyl, triphenylmethyl, 2,4-dimethoxybenzyl, p-methoxybenzyl, benzyl and the like; preferably tert-butoxycarbonyl, benzyloxycarbonyl, fluorenylmethyloxycarbonyl, allyloxycarbonyl, trimethylsilylethoxycarbonyl, methoxycarbonyl, ethoxycarbonyl; more preferably tert-butoxycarbonyl.

Preferably, the method further comprises the steps of:
adding A8 or B8 (1 molar equivalent) into the reaction solvent, adding or dropping deprotection reagent under stirring, stirring at room temperature for 2-4 hours, and after the reaction is completed, spinning the reaction solution to obtain crude product,
then triethylamine (1-3 molar equivalent, for example 1 molar equivalent) is added, stirred, and then (1-2 molar equivalents, e.g. 1.1 molar equivalents) and HATU (1-2 molar equivalents, e.g. 1.1 molar equivalents) are added, and then the reaction solvent is added, triethylamine is added dropwise in an ice water bath, gradually heating up to room temperature, stirring for 1-2 hours, after the reaction is completed, water and the organic solvent are added for extraction, combining organic layers, washing, drying and column chromatography to obtain the compound of general formula I or the compound of general formula I-1;

the deprotection reagent comprises an acidic reagent and a basic reagent, such as hydrobromic acid, hydrochloric acid, trifluoroacetic acid, sodium hydroxide, sodium carbonate, triethylamine and the like; preferably trifluoroacetic acid;

the reaction solvent includes dichloromethane, ethyl acetate, DMF and the like, preferably dichloromethane; the extraction organic solvent is preferably dichloromethane;

the inert atmosphere is preferably a nitrogen atmosphere or an argon atmosphere, and preferably a nitrogen atmosphere.

On the other hand, in the embodiment, the preparation method further comprises the following steps:

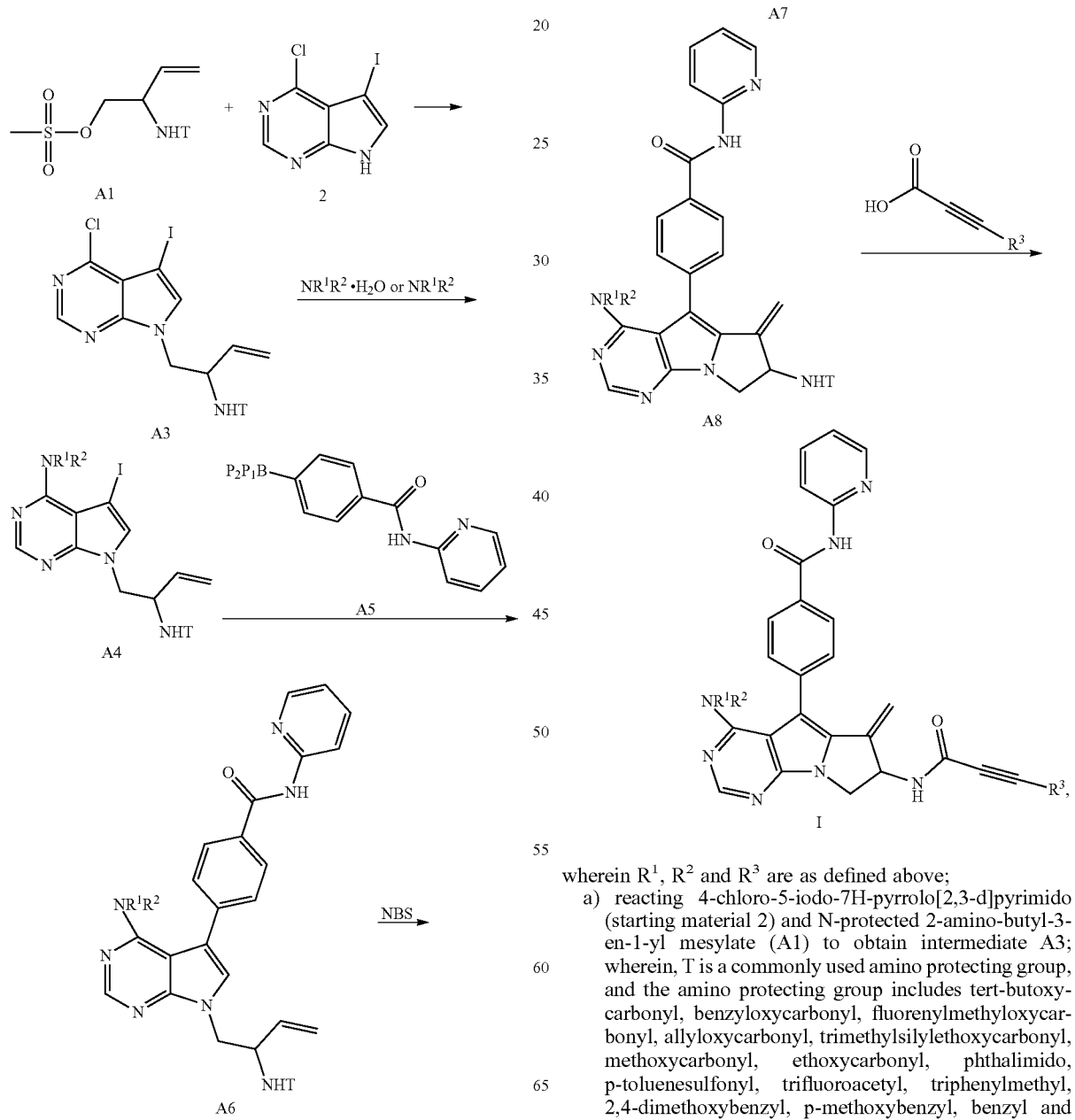

wherein $R^1$, $R^2$ and $R^3$ are as defined above;

a) reacting 4-chloro-5-iodo-7H-pyrrolo[2,3-d]pyrimido (starting material 2) and N-protected 2-amino-butyl-3-en-1-yl mesylate (A1) to obtain intermediate A3; wherein, T is a commonly used amino protecting group, and the amino protecting group includes tert-butoxycarbonyl, benzyloxycarbonyl, fluorenylmethyloxycarbonyl, allyloxycarbonyl, trimethylsilylethoxycarbonyl, methoxycarbonyl, ethoxycarbonyl, phthalimido, p-toluenesulfonyl, trifluoroacetyl, triphenylmethyl, 2,4-dimethoxybenzyl, p-methoxybenzyl, benzyl and the like; preferably tert-butoxycarbonyl, benzyloxycarbonyl, fluorenylmethyloxycarbonyl, allyloxycarbonyl, trimethylsilylethoxycarbonyl, methoxycarbonyl, ethoxycarbonyl; more preferably tert-butoxycarbonyl;

b) reacting intermediate A3 with $NR^1R^2 \cdot H_2O$ or $NR^1R^2$ to obtain intermediate A4;

(c) reacting intermediate A4 with substituted phenylboronic acid or borate ester (A5) to obtain intermediate A6; wherein, $-BP_1P_2$ is $-B(OH)_2$ or

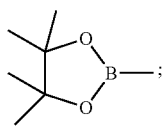

preferably

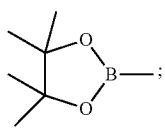

d) reacting intermediate A6 with N-bromosuccinimide (NBS) to obtain intermediate A7;

e) the intermediate A7 is carried out ring-closing reaction to obtain intermediate A8;

f) removing the protective group T from the intermediate A8, and then reacting with

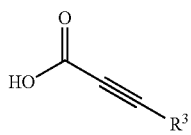

to obtain the compound of general formula I.

Preferably, the compound prepared by the above method is an optical isomer thereof, and in the method:

the steps are the same as those in steps a) to f) above except that the N-protected 2-amino-butyl-3-en-1-yl mesylate (A1) is replaced by the N-protected 2-amino-butyl-3-en-1-yl (S)-mesylate (B1) in the step a):

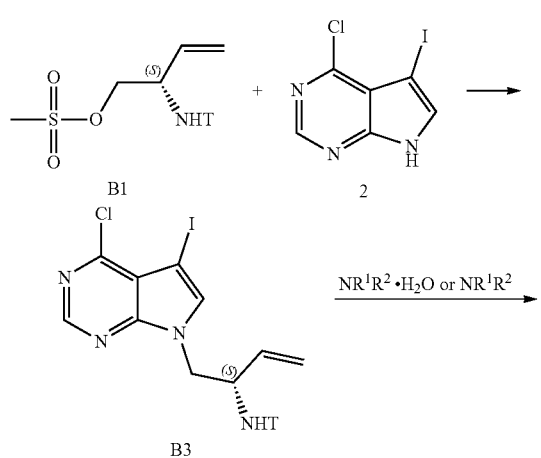

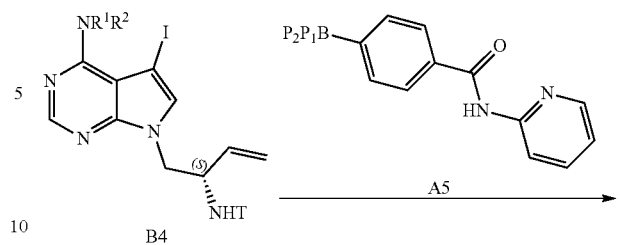

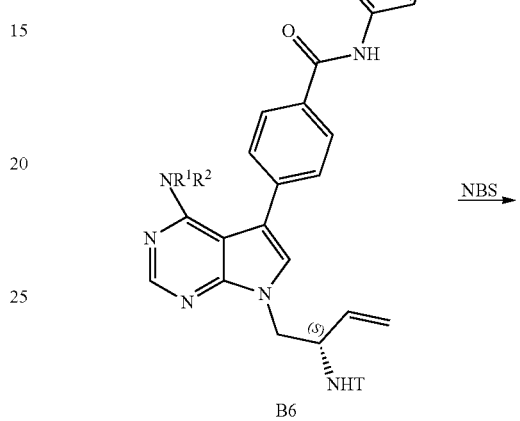

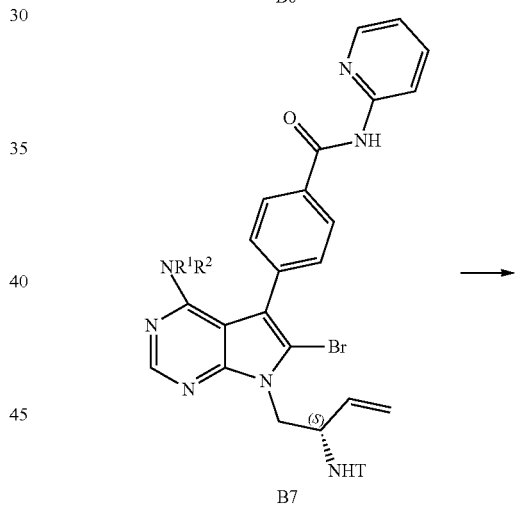

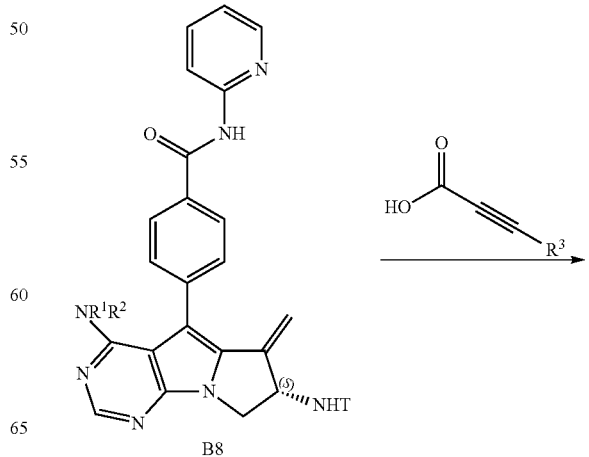

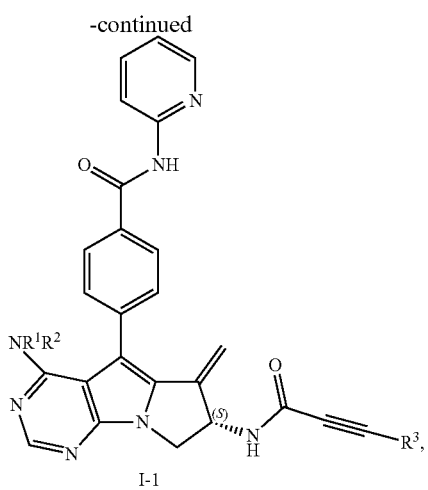

wherein $R^1$, $R^2$, $R^3$, T, $P_1$ and $P_2$ are as defined above.

Further preferably, in an embodiment, the method comprises the following steps:
a) adding dried 4-chloro-5-iodo-7H-pyrrolo[2,3-d]pyrimido (starting material 2) (1 molar equivalent) and anhydrous potassium carbonate (1.5-2.5 molar equivalents, e.g. 2 molar equivalents) into the reaction solvent, followed by the addition of pulverized N-protected 2-amino-butyl-3-en-1-yl mesylate (A1) (1.1-2 molar equivalents, e.g. 1.5 molar equivalents), heating and stirring for 9-15 hours under an inert atmosphere at 50-60° C.,
after the reaction is completed, adding water and organic solvent for extraction, combining organic layers, drying, and column chromatography to obtain intermediate A3; the reaction solvent includes DMF, DMSO, THF, preferably DMF; the organic solvent for extraction includes dichloromethane, ethyl acetate, preferably ethyl acetate;
b) adding the reaction solvent to intermediate A3 (1 molar equivalent), and then adding $NR^1R^2 \cdot H_2O$ or $NR^1R^2$, sealing and reacting for 2-3 hours at 110-130° C.,
after the reaction is completed, cooling to room temperature, adding water and organic solvent for extraction, combining organic layers, washing, drying, and column chromatography separation to obtain intermediate A4; wherein, the reaction solvent includes 1,4-dioxane, THF, preferably 1,4-dioxane; the organic solvent for extraction comprises dichloromethane, ethyl acetate, preferably ethyl acetate;
c) mixing intermediate A4 (1 molar equivalent) with substituted phenylboronic acid or borate ester (A5) (1.2-2 molar equivalents, e.g. 1.4 molar equivalents), adding palladium catalyst (0.1-1 molar equivalent, e.g. 0.2 molar equivalent), adding the reaction solvent, adding sodium carbonate solution under stirring in an inert atmosphere, and refluxing and stirring for 4-6 hours at 80-100° C.,
after the reaction is completed, adding water and the organic solvent for extraction, combining organic layers, washing, drying, column chromatography separation, and recrystallization to obtain intermediate A6; the palladium catalyst comprises Pd ($PPh_3$)$_4$, $PdCl_2$, $PdCl_2$(dppf), Pd(OAc)$_2$ and Pd($PPh_3$)$_2Cl_2$, preferably Pd($PPh_3$)$_4$; the reaction solvent comprises one or more mixed solvents of 1,4-dioxane, THF, ethanol, toluene, methanol, DMF and water, preferably 1,4-dioxane; the organic solvent for extraction comprises dichloromethane, ethyl acetate, preferably ethyl acetate;
d) adding intermediate A6 (1 molar equivalent), N-bromosuccinimide (NBS) (1.0-1.5 molar equivalent, e.g. 1.1 molar equivalents) to the reaction solvent, stirring overnight at room temperature,
after the reaction is completed, adding water and organic solvent for extraction, combining organic layers, washing, drying and column chromatography to obtain intermediate A7; the reaction solvent comprises DMF, THF, acetonitrile and the like, preferably DMF; the organic solvent for extraction comprises dichloromethane, ethyl acetate, preferably ethyl acetate;
e) mixing intermediate A7 (1 molar equivalent) with the palladium catalyst (0.1-0.5 molar equivalent, e.g. 0.11 molar equivalent), adding the reaction solvent, adding sodium hydroxide solution under stirring in an inert atmosphere, refluxing and stirring for 12-18 hours at a temperature of 80-90° C.,
after the reaction is completed, adding water and organic solvent for extraction, combining organic layers, washing, drying and column chromatography to obtain intermediate A8; the palladium catalyst comprises Pd($PPh_3$)$_4$, $PdCl_2$, $PdCl_2$(dppf), Pd(OAc)$_2$ and Pd($PPh_3$)$_2Cl_2$, preferably $PdCl_2$(dppf); the reaction solvent comprises one or more mixed solvents of 1,4-dioxane, THF, ethanol, toluene, methanol, DMF and water, preferably THF; the organic solvent for extraction comprises dichloromethane, ethyl acetate, preferably ethyl acetate;
(f) adding intermediate A8 (1 molar equivalent) into the reaction solvent, adding or dropping the deprotection reagent under stirring, stirring for 2-4 hours at room temperature, and after the reaction is completed, spinning the reaction solution to obtain a crude product,
then triethylamine (1-3 molar equivalents, for example 1 molar equivalent) is added, stirred, and then

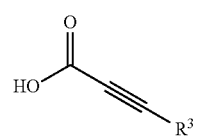

(1-2 molar equivalents, e.g. 1.1 molar equivalents) and HATU (1-2 molar equivalents, e.g. 1.1 molar equivalents) are added, adding solvent, adding triethylamine dropwise in an ice water bath, gradually heating up to room temperature, stirring for 1-2 hours,
after the reaction is completed, water and organic solvent are added for extraction, organic layers are combined, washed, dried, and column chromatography separation to obtain the compound of general formula I; the deprotection reagent comprises an acidic reagent and a basic reagent, such as hydrobromic acid, hydrochloric acid, trifluoroacetic acid, sodium hydroxide, sodium carbonate, triethylamine and the like; preferably trifluoroacetic acid; the reaction solvent includes dichloromethane, ethyl acetate, DMF and the like, preferably dichloromethane; the organic solvent for extraction comprises dichloromethane, ethyl acetate, preferably dichloromethane;
the amount of the reaction solvent and the liquid reactant not specified in specific amount is a conventional amount, for example, the volume of the reaction solvent and the liquid reactant is 100-100000 mL/mol for 1 molar equivalent of the reactant based on 1 molar equivalent of the reactant in each reaction.

The inert atmosphere is preferably a nitrogen atmosphere or an argon atmosphere, and preferably a nitrogen atmosphere.

Further preferably, the compound prepared by the method is an optical isomer thereof, and in the method:

the steps of the process are the same as those in steps a) to f) above except N-protected 2-amino-butyl-3-en-1-yl mesylate (A1) is replaced by the N-protected 2-amino-butyl-3-en-1-yl (S)-mesylate (B1) in the step a), and finally a compound of general formula I-1 is obtained.

In this preparation method and in the present invention, the terms used are as follows:

9-BBN: 9-borabicyclo[3.3.1]nonane
DCM: Dichloromethane
DIAD: Diisopropyl azodicarboxylate
DIPEA: Diisopropyl ethylamine
DMF: N,N-dimethylformamide
EA: Ethyl acetate
HATU: 2-(7-oxidized benzotriazole)-N,N,N',N'-tetramethylurea hexafluorophosphate
NBS: N-bromosuccinimide
NIS: N-iodosuccinimide
PdCl$_2$(dppf): [1,1'-bis(diphenylphosphino) ferrocene]palladium dichloride
Pd (PPh$_3$)$_4$: Tetra (triphenylphosphine) palladium
PdCl$_2$: Palladium dichloride
Pd (OAc)$_2$: Palladium acetate
Pd (PPh$_3$)$_2$Cl$_2$: Bis(triphenyl) phosphate palladium dichloride
PE: Petroleum ether
THF: Tetrahydrofuran
DMSO: Dimethyl sulfoxide The above-described conditions of the process for preparing compounds of formula I or formula I-1, such as reactants, solvents, acids or bases, catalysts, condensing agents, amounts of compounds used, reaction temperatures, time required for the reaction, etc. are not limited to the above explanation. The compounds of the present invention may also be conveniently prepared by optionally combining various synthetic methods described in the specification or known in the art, and such combinations are readily made by those skilled in the art to which the present invention pertains.

According to yet another embodiment of the invention, it provides a pharmaceutical composition comprising a therapeutically effective amount of the compound, pharmaceutically acceptable salts, enantiomers, diastereomers, optical isomers, racemates, deuterated derivatives, solvates or hydrates thereof, and comprising one or more pharmaceutically acceptable carriers. The carrier may include a solid carrier as well as a liquid carrier.

The pharmaceutical composition preferably contains active ingredients in a weight ratio of 1 to 99%, and the preferred ratio is the compound, pharmaceutically acceptable salt, enantiomer, diastereomer, optical isomer, racemate, deuterated derivative, solvate or hydrate thereof as active ingredient accounts for 65% to 99% of the total weight, and the remainder is, for example, a pharmaceutically acceptable carrier.

The compound and pharmaceutical composition of the present invention may be in various forms, such as tablets, capsules, powders, syrups, solutions, suspensions, aerosols, etc. and may be present in suitable solid or liquid carriers or diluents and in suitable sterilizing appliances for injection or drip.

Various dosage forms of the pharmaceutical composition can be prepared according to conventional preparation methods in the pharmaceutical field. The formulation contains 0.05 to 1000 mg of the compound in a unit dose, preferably 0.1 to 500 mg of the compound in a unit dose of the formulation.

The compound and pharmaceutical composition of the present invention can be used clinically in mammals, including humans and animals, and can be administered through oral, nasal, dermal, pulmonary, or gastrointestinal routes of administration. It is most preferably administered orally. Preferably, the daily dose is 0.01-1000 mg/kg body weight, taken at one time, or 0.01-500 mg/kg body weight, taken in divided doses. Regardless of the method of administration, the individual's optimal dosage should be determined based on the specific treatment. Normally, start with a small dose and gradually increase the dose until the most suitable dose is found.

According to yet another embodiment of the present invention, it provides a use of the compound, pharmaceutically acceptable salts, enantiomers, diastereomers, optical isomers, racemates, deuterated derivatives, solvates or hydrates thereof in the preparation of a medicament for the treatment of diseases associated with the BTK kinase signal transduction pathway.

According to yet another embodiment of the invention, it provides the compound, pharmaceutically acceptable salts, enantiomers, diastereomers, optical isomers, racemates, deuterated derivatives, solvates or hydrates thereof, for the treatment of diseases associated with the BTK kinase signal transduction pathway or for the preparation of a medicament for the treatment of diseases associated with the BTK kinase signal transduction pathway.

According to yet another embodiment of the invention, it provides a method for treating a disease associated with a BTK kinase signal transduction pathway, wherein a therapeutically effective amount of the compound, pharmaceutically acceptable salt, enantiomer, diastereomer, optical isomer, racemate, deuterated derivative, solvate or hydrate thereof is administered to a subject.

In which, the diseases associated with the BTK kinase signal transduction pathway include cancer, hyperplasia, restenosis, immune disorders and inflammation.

According to yet another embodiment of the invention, it provides a use of the compound, pharmaceutically acceptable salts, enantiomers, diastereomers, optical isomers, racemates, deuterated derivatives, solvates or hydrates thereof in the preparation of a medicament for the treatment, prevention or regulation of cancer.

According to yet another embodiment of the invention, it provides the compound, pharmaceutically acceptable salts, enantiomers, diastereomers, optical isomers, racemates, deuterated derivatives, solvates or hydrates thereof for the treatment, prevention or regulation of cancer or for the preparation of a medicament for the treatment, prevention or regulation of cancer.

According to yet another embodiment of the invention, it provides a method of treating, preventing or regulating cancer, wherein a therapeutically effective amount of the compound, pharmaceutically acceptable salt, enantiomer, diastereomer, optical isomer, racemate, deuterated derivative, solvate or hydrate thereof is administered to a subject.

The cancer of the invention comprises hematological tumors and solid tumors; wherein, the hematological tumors include lymphoma, myeloma and leukemia; preferably, the cancer includes, but is not limited to, histiocytic lymphoma, mantle cell lymphoma, diffuse large B cell lymphoma, chronic lymphocytic leukemia, ovarian cancer, phosphoepithelial cell carcinoma of head and neck, gastric cancer, breast cancer, hepatocellular carcinoma in children, colorectal cancer, cervical cancer, lung cancer, sarcoma, nasopharyngeal cancer, pancreatic cancer, glioblastoma, prostate cancer, small cell lung cancer, non-small cell lung cancer, multiple myeloma, thyroid cancer, testicular cancer, cervical cancer, endometrial cancer, esophageal cancer, renal cell cancer, bladder cancer, lung adenocarcinoma, liver cancer and astrocytoma; preferably mantle cell lymphoma, diffuse large B cell lymphoma, chronic lymphocytic leukemia, phosphoepithelial cell carcinoma of head and neck, histiocytic lymphoma, lung adenocarcinoma, small cell lung cancer, non-small cell lung cancer, pancreatic cancer, papillary renal cell carcinoma, liver cancer, gastric cancer, colon cancer, multiple myeloma and glioblastoma.

According to the experiment of the invention, the inhibitory activity of the compound of the invention for BTK at the molecular level and the cell level is equal to or better than that of the marketed drug ibrutinib or other control compounds. Importantly, the compound of the invention has higher activity to Ramos cells and TMD8 cells of human diffuse large B lymphoma sensitive to BTK, especially TMD8 cells, which can be taken orally, and the activity in mice is significantly better than that of ibrutinib, and has good metabolic stability. It is a selective inhibitor of BTK with development potential, and can be used as a candidate drug for preclinical and clinical research.

DETAILED DESCRIPTION OF THE INVENTION

Figure 1:
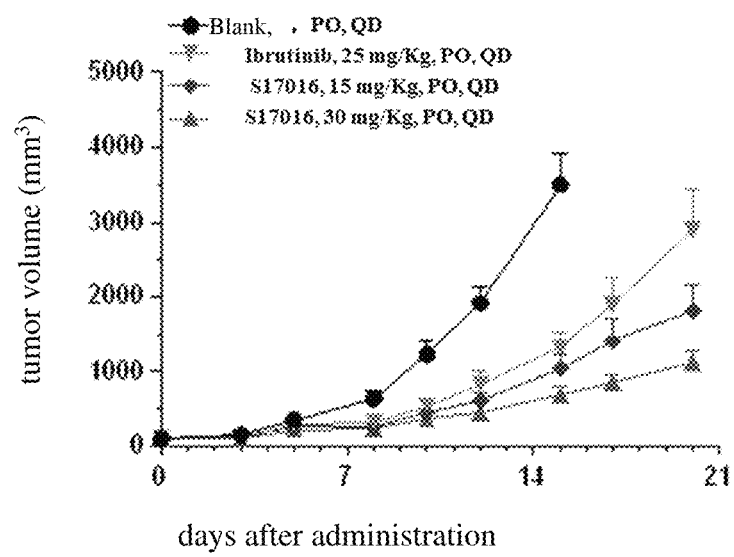
FIG. 1: Schematic diagram of experimental results of REC-1 xenograft tumor model.

To enable those having ordinary knowledge in the art to understand the features and effects of the present invention, a general description and definition of the terms and expressions referred to in the specification and the scope of the patent application are given below. Unless otherwise indicated, all technical and scientific terms used herein have a general meaning to those skilled in the art with regard to the invention and, in the event of a conflict, the definitions herein shall prevail.

In this context, the terms "contain", "include", "have", "comprise" or any other similar terms are open-ended transitional phrases intended to encompass non-exclusive inclusions. For example, a composition or article containing plural elements is not limited to the elements listed herein, but may also include other elements not explicitly listed but typically inherent in the composition or article. In addition, unless expressly stated to the contrary, the term "or" refers to an inclusive "or", not an exclusive "or". For example, the condition "A or B" is satisfied in any of the following cases: A is true (or exists) and B is false (or does not exist), A is false (or does not exist) and B is true (or exists), and both A and B are true (or exist). In addition, in this context, the terms "comprise (comprising)", "include (including)", "have (having)" and "contain (containing)" shall be interpreted as specifically disclosed and cover both closed or semi-closed conjunctions such as "composed of" and "substantially composed of".

In this context, all features or conditions defined in the form of numerical ranges or percentage ranges are for simplicity and convenience only. Accordingly, descriptions of numerical ranges or percentage ranges should be deemed to cover and specifically disclose all possible sub-ranges and individual values within ranges, in particular integer values. For example, a range description of "1 to 8" shall be deemed to have specifically disclosed all sub-ranges such as 1 to 7, 2 to 8, 2 to 6, 3 to 6, 4 to 8, 3 to 8, in particular sub-ranges defined by all integer values, and shall be deemed to have specifically disclosed individual values such as 1, 2, 3, 4, 5, 6, 7, 8 within the range. Unless otherwise indicated, the foregoing explanation method applies to all contents of the present invention regardless of its scope.

If a quantity or other value or parameter is expressed in terms of a range, a preferred range, or a series of upper and lower limits, it shall be understood to mean that all ranges consisting of any pair of upper or better values of such range and lower or better values of such range have been specifically disclosed herein, whether or not these ranges are separately disclosed. In addition, when a range of values is mentioned in this context, it should include its endpoints and all integers and fractions within the range unless otherwise stated.

In this context, a numerical value is understood to have an accuracy of the number of significant digits of the numerical value provided that the object of the invention can be achieved. For example, the number 40.0 should be understood to cover the range from 39.50 to 40.49.

In this context, in cases where a Markush group or optional term is used to describe a feature or example of the invention, it will be understood by those skilled in the art that a subgroup of all elements or any individual element within a Markush group or an optional list may also be used to describe the invention. For example, if X is described as "selected from the group consisting of $X_1$, $X_2$ and $X_3$", it also means that the claim that X is $X_1$ and the claim that X is $X_1$ and/or $X_2$ have been fully described. Furthermore, in cases where Markush group or optional term are used to describe features or examples of the invention, those skilled in the art will appreciate that any combination of subgroups or individual elements of all elements within a Markush group or optional list may also be used to describe the invention. Accordingly, for example, if X is described as "selected from the group consisting of $X_1$, $X_2$ and $X_3$", and Y is described as "selected from the group consisting of $Y_1$, $Y_2$ and $Y_3$", it means that the claim that X is $X_1$ or $X_2$ or $X_3$ and Y is $Y_1$ or $Y_2$ or $Y_3$ has been fully described.

The starting materials, reaction reagents, catalysts or solvents referred to in the following embodiments are commercially available or prepared by conventional methods in the prior art.

The following specific embodiments are merely illustrative in nature and are not intended to limit the present invention and its use. Furthermore the present invention is not limited by any of the theories described in the foregoing prior art or summary of the invention or the following specific embodiments or examples.

Preparation Example 1: Synthesis of S17016

1. Synthesis of Intermediate 3

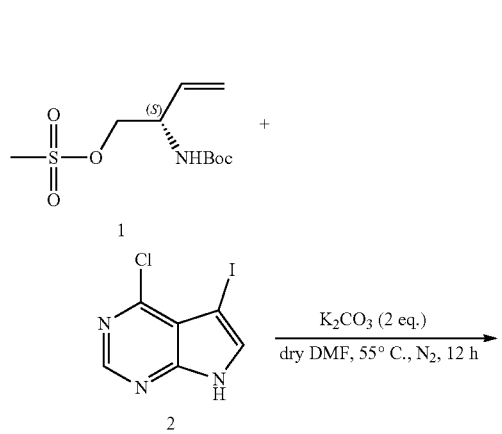

4-chloro-5-iodo-7H-pyrrolo[2,3-d]pyrimido (starting material 2, 17.28 g, 1 eq) and anhydrous potassium carbonate (2 eq) were added into a 250 mL round-bottom flask, and water was removed by vacuum drying. Dry DMF was added as a solvent, crushed 2-((tert-butoxycarbonyl)amino)-butyl-3-en-1-yl (S)-mesylate(starting material 1, 24.6 g, 1.5 eq) was added, and replaced with $N_2$. Heating and stirring for 12 hours at 55° C., and the time can be extended to ensure complete reaction.

After the reaction was completed, water and ethyl acetate were added for extraction for three times, the ester layers were combined, water was used for reverse phase extraction once, and washed with saturated salt water. Dried with anhydrous sodium sulfate. Dry column chromatography (eluent: $CHCl_3$:MeOH=100:1) to obtain the product (S)-(1-(4-chloro-5-iodo-7H-pyrrolo[2,3-d]pyrimido-7-yl) but-3-en-2-yl) tert-butyl carbamate (Intermediate 3, 19.28 g) in a yield of 69.5%.

$^1$H NMR (300 MHz, $CDCl_3$) δ 8.60 (s, 1H), 7.39 (s, 1H), 5.82 (ddd, J=17.1, 10.5, 5.5 Hz, 1H), 5.33-5.14 (m, 2H), 4.80 (s, 1H), 4.63-4.51 (m, 1H), 4.51-4.42 (m, 1H), 4.35 (s, 1H), 1.33 (s, 9H). ee>99.5%.

2. Synthesis of Intermediate 4

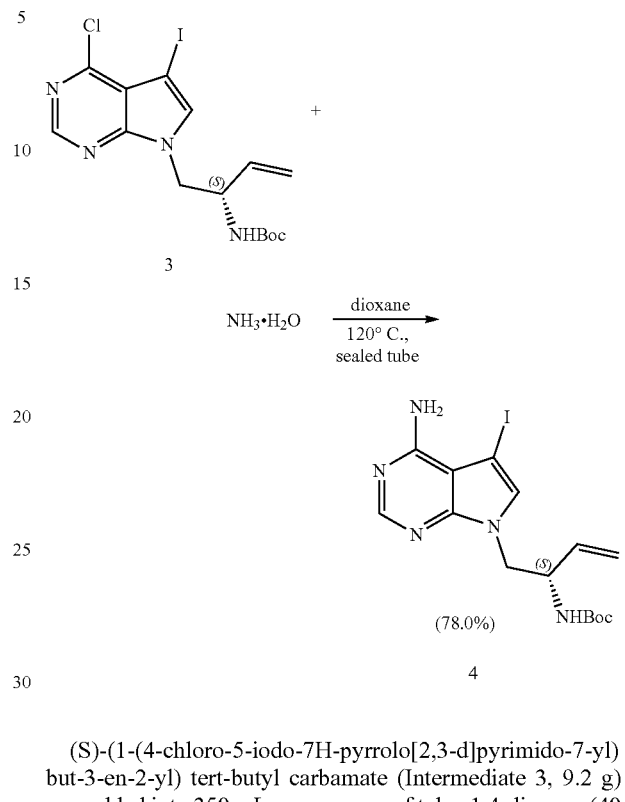

(S)-(1-(4-chloro-5-iodo-7H-pyrrolo[2,3-d]pyrimido-7-yl) but-3-en-2-yl) tert-butyl carbamate (Intermediate 3, 9.2 g) was added into 350 mL pressure-proof tube, 1,4-dioxane (40 mL) was added as a solvent, and ammonia water (40 mL) was added. The reaction was sealed at 120° C. for 2.5 hours.

After the reaction was completed, cooled to room temperature, water and ethyl acetate were added for extraction, ester layers were combined, and washed with saturated salt water. Dried with anhydrous sodium sulfate. Dry column chromatography (eluent: $CHCl_3$:MeOH=30:1) to obtain the product (S)-(1-(4-amino-5-iodo-7H-pyrrolo[2,3-d]pyrimido-7-yl) but-3-en-2-yl) tert-butyl carbamate (Intermediate 4, 6.86 g) in a yield of 78.0%.

$^1$H NMR (300 MHz, $CDCl_3$) δ 8.25 (s, 1H), 7.05 (s, 1H), 5.87-5.74 (m, 1H), 5.72 (s, 2H), 5.34-5.13 (m, 3H), 4.56-4.43 (m, 1H), 4.34 (dd, J=14.8, 4.9 Hz, 1H), 4.30-4.15 (m, 1H), 1.35 (s, 9H). ee>99.5%.

3. Synthesis of Intermediate 6

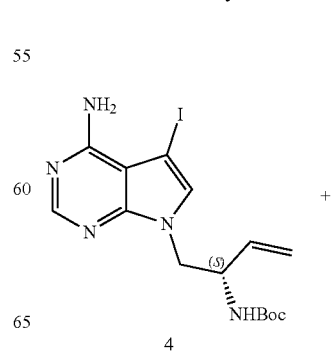

4. Synthesis of Intermediate 7

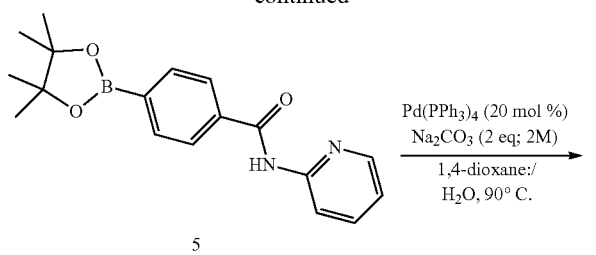

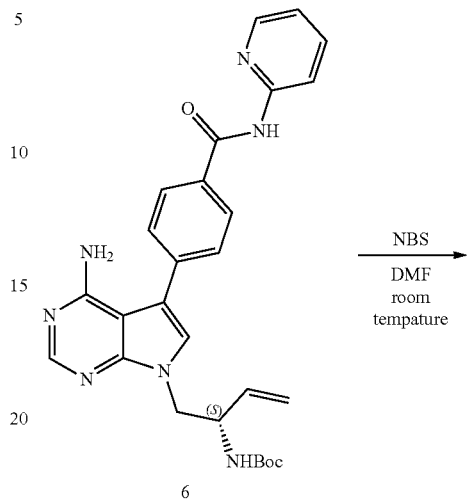

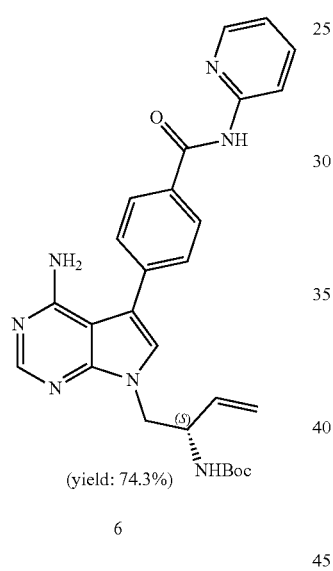

(yield: 74.3%)

6

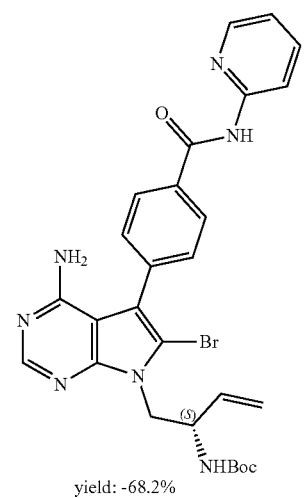

yield: ~68.2%

7

(S)-(1-(4-amino-5-iodo-7H-pyrrolo[2,3-d]pyrimido-7-yl) but-3-en-2-yl) tert-butyl carbamate (Intermediate 4, 32.9 g, 1 eq), N-(pyridin-2-yl)-4-(4,4,5,5-tetramethyl-1,3,2-dioxaborolan-2-yl)benzamide (starting material 5, 34.8 g, 1.4 eq) and Pd(PPh$_3$)$_4$ (17.7 g, 0.2 eq) were added into a 1 L round bottom flask. 1,4-dioxane (383 mL) was added as a solvent and replaced with N$_2$. 2M sodium carbonate solution (76.6 mL) was added with stirring. Stirred under reflux at 90° C. for 5 hours.

Water and ethyl acetate were added for extraction, and the ester layers were combined and washed with saturated brine. Dried with anhydrous sodium sulfate. Dry column chromatography, EA was used as eluent to remove most impurities, and then a mixture of CHCl$_3$:MeOH=30:1 was used as eluent. Product may contain a small amount of impurities, PE can be used for recrystallization to precipitate pure product. The product (S)-(1-(4-amino-5-(4-(pyridin-2-ylcarbamoyl) phenyl)-7H-pyrrolo[2,3-d]pyrimido-7-yl][but-3-en-2-yl]tert-butyl carbamate (Intermediate 6, 28.4 g) was obtained in a yield of 74.3%. ee>99.5%.

(S)-(1-(4-amino-5-(4-(pyridin-2-ylcarbamoyl) phenyl)-7H-pyrrolo[2,3-d]pyrimido-7-yl) but-3-en-2-yl) tert-butyl carbamate (Intermediate 6, 32.7 g, 1 eq) was added into a 1 L round bottom flask, 600 mL DMF was added as solvent. NBS (12.8 g, 1.1 eq) was slowly added under stirring and stirred overnight at room temperature.

After the reaction was completed, water and ethyl acetate were added for extraction, ester layers were combined, water was added for reverse phase extraction once, and washed with saturated salt water. Dried with anhydrous sodium sulfate. Dry column chromatography, a mixture of CHCl$_3$:MeOH=50:1 was used firstly as an eluent, then a mixture of CHCl$_3$:MeOH 30:1 was used as an eluent. The product(S)-(1-(4-amino-6-bromo-5-(4-(pyridin-2-ylcarbamoyl) phenyl)-7H-pyrrolo[2,3-d]pyrimido-7-yl][but-3-en-2-yl]tert-butyl carbamate(Intermediate 7, 25.8 g) was obtained in a yield of 68.2%. ee>99.5%.

5. Synthesis of Intermediate 8

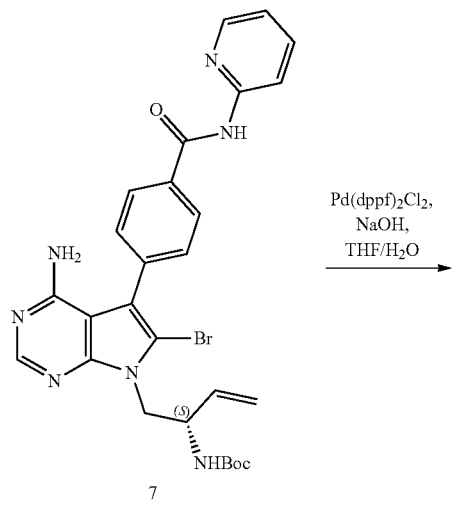

(S)-1-(4-amino-6-bromo-5-(4-(pyridin-2-ylcarbamoyl) phenyl)-7H-pyrrolo[2,3-d]pyrimido-7-yl)but-3-en-2-yl) tert-butyl carbamate (Intermediate 7, 11.9 g, 1 eq) and PdCl₂(dppf) (1.66 g, 0.11 eq) were added into a 250 mL round bottom flask, 51 mL THF was added as solvent and replaced with N₂ for several times to ensure completeness. 4 M sodium hydroxide solution (8.2 ml) was added under stirring. Stirred under reflux for 15 hours at 85° C.

After the reaction was completed, water and ethyl acetate were added for extraction, the ester layers were combined, and washed with saturated salt water. Dried with anhydrous sodium sulfate. Dry column chromatography (eluent: CHCl₃:MeOH=30:1) to obtain (S)-(4-amino-6-methylene-5-(4-(pyridin-2-ylcarbamoyl) phenyl)-7, 8-dihydro-6H-pyrimido[5,4-b]pyrrolizin-7-yl) tert-butyl carbamate (Intermediate 8, 8.79 g) in a yield of 85.9%. ee>99.5%.

6. Synthesis of S17016

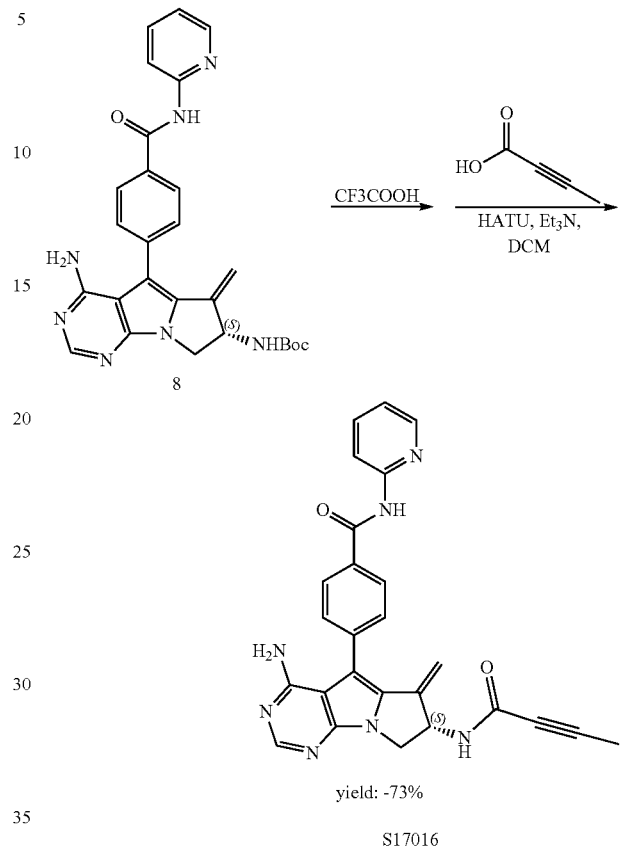

yield: ~73%

S17016

(S)-(4-amino-6-methylene-5-(4-(pyridin-2-ylcarbamoyl) phenyl)-7, 8-dihydro-6H-pyrimido[5,4-b]pyrrolizin-7-yl) tert-butyl carbamate (Intermediate 8, 2.75 g, 1 eq), 110 mL DCM was added as solvent. Trifluoroacetic acid (10.5 ml) was added dropwise under stirring. Stirred at room temperature for 3 hours. After the reaction was finished, the reaction solution was directly spun dry, and the trifluoroacetic acid was taken out with methanol for several times. After spinning dry, the amino Boc-deprotected crude product was obtained, which was directly used in the next step.

The product from the previous step was transferred to a 50 mL round bottom flask, and triethylamine (1 eq) was added, stirred for five minutes, followed by 2-butynoic acid (0.511 g, 1.1 eq) and HATU (2.31 g, 1.1 eq), 100 mL DCM was added as solvent. Cooled to 0° C. with the ice water bath, triethylamine (1.54 mL+0.77 mL) was added dropwise. Gradually heated up to room temperature and stirred at room temperature for 1.5 hours. The reaction solution was yellowish. Water and DCM were added for extraction, organic phases were combined, and washed with saturated salt water. Dried with anhydrous sodium sulfate and column chromatography (CHCl₃:MeOH=30:1), the final product 517016 (1.88 g) was obtained in a yield of 73.3%. ee>99.5%.

1H NMR (400 MHz, CDCl₃) 8.98 (s, 1H), 8.43 (dt, J=8.3, 1.0 Hz, 1H), 8.34 (ddd, J=5.0, 1.9, 0.9 Hz, 1H), 8.22 (s, 1H), 8.09-8.03 (m, 2H), 7.81 (ddd, J=8.4, 7.4, 1.9 Hz, 1H), 7.69-7.63 (m, 2H), 7.13 (ddd, J=7.4, 4.9, 1.0 Hz, 1H), 6.55 (d, J=8.2 Hz, 1H), 5.67 (m, J=8.1, 5.7, 2.6 Hz, 1H), 5.56 (d, J=2.3 Hz, 1H), 5.40 (s, 2H), 5.27 (d, J=2.3 Hz, 1H), 4.70 (dd, J=11.7, 8.1 Hz, 1H), 4.09-3.99 (m, 1H), 1.99 (s, 3H).

Experimental Example 1: Inhibitory Activity Evaluation of Bruton Kinase (BTK) at Molecular Level The enzyme reaction substrate Poly (Glu, Tyr)$_{4:1}$ was diluted with potassium-free PBS (10 mM sodium phosphate buffer, 150 mM NaCl, pH 7.2-7.4) to 20 μg/ml, and coated enzyme plate. After reacting at 37° C. for 12-16 hours, the plate was washed three times with 200 μL/well T-PBS (PBS containing 0.1% Tween-20) and dried in 37° C. oven for 1-2 hours. 49 μL/well ATP solution (final concentration was 5 μM) diluted with a reaction buffer (50 mM HEPES pH 7.4, 50 mM MgCl$_2$, 0.5 mM MnCl$_2$, 0.2 mM Na$_3$VO$_4$, 1 mM DTT) was firstly added into the substrate-coated plate. 1 μL compound to be tested (compound well) or DMSO with corresponding concentration (negative control well) was added into each well, and enzyme-free control well was set up for each experiment. Then 50 μL of BTK tyrosine kinase protein diluted with reaction buffer was added to start the reaction.

The above reaction system was placed in a shaking table (100 rpm) for 1 hour at 37° C., then the plate was washed with T-PBS for three times, and the primary antigen PY99 100 μL/well (Santa Cruz) was added, and the reaction was carried out in a shaking table for 0.5 hours at 37° C. After washing the plate with T-PBS, 100 μL/well of HRP labeled goat anti-mouse secondary antibody diluent was added, and the reaction was carried out in a shaking table for 0.5 hours at 37° C. After washing the plate with T-PBS, 2 mg/mL OPD chromogenic solution 100 μL/well was added, and reacted at 25° C. for 1-10 minutes without light. Then the reaction was suspended by adding 50 μL/well 2 M H$_2$SO$_4$, and the readings were made by microplate enzyme-labeled instrument SPECTRA MAX Plus 384 with adjustable wavelength at 490 nm.

Compounds S1, S10, Ibrutinib and Acalabrutinib were used as positive control compounds, wherein compounds S1 and S10 were prepared using the methods disclosed in the prior art (e.g. CN108101905A) or the like, Ibrutinib and Acalabrutinib were purchased from Selleck.

The inhibition rate of each compound was obtained by the following formula:

$$\text{inhibition rate } \% = \left(1 - \frac{\text{compound}_{OD\,value} - \text{enzyme-free control}_{OD\,value}}{\text{negative control}_{OD\,value} - \text{enzyme-free control}_{OD\,value}}\right) \times 100\%$$

The IC$_{50}$ value was obtained by four-parameter regression using the software attached to the microplate reader. The results are listed in Table 1 below.

TABLE 1

| Compound | IC$_{50}$ (nM) |
|---|---|
| S1 | ~1 |
| S10 | <10 |
| Ibrutinib | ~1 |
| Acalabrutinib | ~10 |
| S17016 | 0.5 |

The above results indicated that the inhibitory activity of compound S17016 on BTK was superior to that of previous compounds S1 and S10, and also superior to the first generation BTK inhibitor Ibrutinib and the second generation BTK inhibitor Acalabrutinib.

Experimental Example 2: Inhibitory Activity of the Compound on the Proliferation of Human B Lymphoma Cell Ramos (Burkitt Lymphoma) and Human Diffuse Large B Lymphoma Cell TMD8 In Vitro Cell suspensions (Ramos: 10000 cells/well; TMD8: 12000 cells/well) were seeded in a 96-well plate, placed in an incubator for 2 hours at 37° C., after the cell state was stabilized, different concentrations of tested compounds were added to each well (each concentration was set with 3 duplicate wells), and blank control (only containing culture solution, but not containing cells), negative control (only adding cells, but not adding compounds) and positive compound control were set at the same time. After 72 h treatment, 20 μL MTT (5 mg/ml) was added to each well and incubated for 4 h at 37° C. 100 μL triple solution (10% SDS, 5% isobutanol, 0.01 M HCl) was added and placed overnight at 37° C. The OD value was measured with microplate enzyme-labeled instrument SPECTRA MAX Plus 384 with adjustable wavelength at 570 nm.

The inhibition rate of the compound was obtained by the following formula:

$$\text{inhibition rate } \% = \left(1 - \frac{OD_{dosing\,hole} - OD_{blank\,control}}{OD_{negative\,control} - OD_{blank\,control}}\right) \times 100\%$$

The IC$_{50}$ value was obtained by four-parameter regression using the software attached to the microplate reader. The experiment was repeated three times independently, and the results are listed in Table 2 below.

The compounds S1, S10, Ibrutinib, Acalabrutinib, S18s, S19s and S20s described above were also used as positive control compounds.

TABLE 2

| Compound | Ramos cell IC$_{50}$ | TMD8 cell IC$_{50}$ |
|---|---|---|
| S1 | 94.73 μM | 0.006 μM |
| S10 | 8.72 μM | 0.030 μM |
| Ibrutinib | 12.91 μM | 0.005 μM |
| Acalabrutinib | 38.16 μM | 0.023 μM |
| S17016 | 3.15 μM | 0.003 μM |
| S18s | 5.04 μM | 0.016 μM |
| S19s | — | 0.017 μM |
| S20s | 14.3 μM | 0.004 μM |

The above results indicated that the inhibitory ability of compound S17016 on BTK-dependent cell proliferation was superior to that of preceding compounds S1, S10, S18s, S19s and S20s, and also superior to the first generation BTK inhibitor Ibrutinib and the second generation BTK inhibitor Acalabrutinib. It should be further noted that the compound S17016 of the present invention has higher proliferation inhibitory activity for Ramos cells and higher proliferation inhibitory activity for TMD8 cells compared with other compounds.

Experimental Example 3: Evaluation of Anti-Tumor Activity In Vivo

Laboratory Animals:
TMD8 Xenograft Tumor Model
1) Species: Mice
2) Strain: CB-17 SCID
3) Age and body weight: 6-8 weeks; 18-22 g 4) Sex: Female
5) Supplier: Beijing Vital River Laboratory Animal Technology Co., Ltd.

REC-1 Xenograft Tumor Model
1) Species: Mice
2) Strain: BALB/c nude mice
3) Age and body weight: 6-8 weeks; 17-20 g
4) Sex: Female
5) Supplier: Shanghai Lingchang Biotechnology Co., Ltd.

Cell culture: Human lymphoma TMD8 cells were cultured in suspension in vitro with RPMI 1640 medium (Supplier: gibco; Item No.: 22400-089; Production batch No. 4868546) supplemented with 10% fetal bovine serum, 100 U/ml penicillin and 100 µg/ml streptomycin, cultivated at 37° C. with 5% $CO_2$. Conventional treatment was carried out twice a week. When the cell saturation was 80%-90%, the cells were collected, counted and inoculated.

Human mantle cell lymphoma REC-1 cells were cultured in suspension in vitro with RPMI 1640 medium (Supplier: gibco; item No. 22400-089; Production batch No. 1868795) supplemented with 10% fetal bovine serum, 100 U/ml penicillin and 100 µg/ml streptomycin, cultivated at 37° C. with 5% $CO_2$. Conventional treatment was carried out twice a week. When the cell saturation was 80%-90%, the cells were collected, counted and inoculated.

Tumor cell inoculation: 0.2 mL $10 \times 10^6$ Human lymphoma TMD8 cells were subcutaneously inoculated into the right back of each nude mouse (PBS:Matrigel=1:1). When the average tumor volume reached 104 $mm^3$, group administration began. Each group of 6 mice was grouped according to the tumor volume by random grouping software based on Excel.

0.2 mL $5 \times 10^6$ REC-1 cells were subcutaneously inoculated into the right back of each nude mouse (PBS:Matrigel=1:1). When the average tumor volume reached 100 $mm^3$, group administration began. Each group of 6 mice was grouped according to the tumor volume by random grouping software based on Excel.

Preparation of Test Substance:
See Table 3 and Table 4 below for the preparation method of the test substance:

TABLE 3

Preparation Method of Test Substance in TMD8 Xenograft Tumor Model

| Compound | Packing or initial concentration | Preparation method | Concentration (mg/mL) | Storage condition |
|---|---|---|---|---|
| Vehicle | — | 5% DMSO + 95% (20% HP-β-CD) | — | 4° C. |
| S17016 | 71 + 33.5 mg/bottle | 2.7 mg S17016 was weighed and dissolved with 0.135 ml DMSO, and 2.565 ml 20% HP-β-CD was added, and vortex dissolved. Keep away from light. | 1.0 | Freshly prepared just before use |
| S17016 | 71 + 33.5 mg/bottle | 0.9 mL of vehicle was added into 0.9 mL of the prepared S17016 solution with a concentration of 1 mg/mL, and vortex dissolved. Keep away from light. | 0.5 | Freshly prepared just before use |
| Ibrutinib | 1000 mg/bottle | 31.8 mg S17016 was weighed and dissolved with 0.63 mL DMSO, and 11.97 mL 20% HP-β-CD was added, and vortex dissolved. Keep away from light. | 2.5 | 4° C. |

Note:
Before administrating to animals, it is necessary to mix the medicine gently and thoroughly.

TABLE 4

Preparation Method of Test Substance in REC-1 Xenograft Tumor Model

| Compound | Packing or initial concentration | Preparation method | Concentration (mg/mL) | Storage condition |
|---|---|---|---|---|
| Vehicle | — | 5% DMSO + 95% (20% HP-β-CD) | — | 4° C. |
| S17016 | 277 mg/bottle | 2.7 mg SOMCL-17-016 was weighed and dissolved with 0.09 mL DMSO, and 1.71 mL 20% HP-β-CD was added, and vortex dissolved. Keep away from light. | 1.5 | 4° C. |
| S17016 | 277 mg/bottle | 5.4 mg SOMCL-17-016 was weighed and dissolved with 0.09 mL DMSO, and 1.71 mL 20% HP-β-CD was added, and vortex dissolved. Keep away from light. | 3 | 4° C. |
| Ibrutinib | 1000 mg/bottle | 31.8 mg Ibrutinib was weighed and dissolved with 0.63 mL DMSO, and 11.97 mL 20% HP-β-CD was added, and vortex dissolved. Keep away from light. | 2.5 | 4° C. |

Daily observation of experimental animals: The formulation and any modification of this experimental scheme had passed the evaluation and approval of the Institutional Animal Care and Use Committee (IACUC) of Suzhou WuXi PharmaTech New Drug Development Co., Ltd. The use and welfare of laboratory animals were governed by the Association for Assessment and Accreditation of Laboratory Animal Care (AAALAC). The health status and death status of animals were monitored every day. Routine examinations included observing the effects of tumor growth and drug treatment on daily behaviors of animals, such as behavioral activities, food intake and water intake (visual inspection only), weight change (weight measurement three times a week), appearance signs or other abnormal conditions. Based on the number of animals in each group, the number of animal deaths and side effects in each group were recorded.

Tumor measurement and experimental indexes: the experimental index was to investigate whether the tumor growth is inhibited, delayed or cured. The tumor diameter was measured with vernier caliper three times a week.

The formula for calculating tumor volume is:

$$V = 0.5 \times a \times b^2,$$

a and b denote the long and short diameter of the tumor, respectively.

TGI (%) or relative tumor proliferation rate T/C (%) was used to evaluate the antitumor efficacy of the compounds. TGI (%), reflecting the tumor growth inhibition rate.

Calculation of TGI (%):

TGI (%)=[1−(average tumor volume at the end of administration in a treatment group-average tumor volume at the beginning of administration in the treatment group)/(average tumor volume at the end of treatment in vehicle control group-average tumor volume at the beginning of treatment in vehicle control group)]×100%.

Relative tumor proliferation rate T/C (%): the calculation formula is as follows:

T/C %=$T_{RTV}/C_{RTV}$×100% ($T_{RTV}$: Relative tumor volume in treatment group; $C_{RTV}$: Relative tumor volume in negative control group). The relative tumor volume (RTV) was calculated according to the results of tumor measurement, and the formula was RTV=$V_t/V_0$, wherein $V_0$ is the average tumor volume (i.e. $d_0$) when the drug is administered in groups, $V_t$ is the average tumor volume at a certain measurement, $T_{RTV}$ and $C_{RTV}$ are the data of the same day.

Statistical analysis: Statistical analysis, including the mean value of tumor volume and standard error (SEM) at each time point in each group. The treatment group showed the best therapeutic effect on the 15th day (REC-1 xenograft tumor model) and the 17th day (TMD8 xenograft tumor model) after administration, so statistical analysis was carried out to evaluate the differences between the groups based on this data. Three or more groups were compared with one-way ANOVA. If there were significant differences in F values, Games-Howell method was used to test. All data were analyzed with SPSS 17.0. p<0.05 was considered as significant difference.

The in vivo efficacy of compound S17016 in human mantle cell lymphoma REC-1 xenograft model was shown in Table 5 and FIG. 1. The volume of tumor was 3501 mm³ in the solvent control group on the 15th day after administration, Ibrutinib 25 mg/kg group had significant anti-tumor effect compared with solvent control group (T/C=38%, TGI=64%, p=0.008) and the tumor volume was 1323 mm³. The tumor volumes of compound S17016 in 15 mg/kg and 30 mg/kg groups were 1034 mm³ and 680 mm³, respectively. Compared with the vehicle control group, it had a significant anti-tumor effect (T/C values were 30% and 19%, TGI values were 73% and 83%, p=0.004 and 0.003).

TABLE 5

Evaluation of anti-tumor efficacy of S17016 on REC-1 xenograft tumor model (calculated based on tumor volume on the 15th day after administration)

| Group | Tumor volume (mm³)[a] (Day 15) | T/C[b] (%) | TGI[b] (%) | p value[c] |
|---|---|---|---|---|
| Blank control | 3501 ± 412 | — | — | — |
| Ibrutinib (25 mg/kg) | 1323 ± 195 | 38 | 64 | 0.008 |

TABLE 5-continued

Evaluation of anti-tumor efficacy of S17016 on REC-1 xenograft tumor model (calculated based on tumor volume on the 15th day after administration)

| Group | Tumor volume (mm³)[a] (Day 15) | T/C[b] (%) | TGI[b] (%) | p value[c] |
|---|---|---|---|---|
| S17016 (15 mg/kg) | 1034 ± 202 | 30 | 73 | 0.004 |
| S17016 (30 mg/kg) | 680 ± 106 | 19 | 83 | 0.003 |

Note:
[a]Mean ± SEM;
[b]Tumor growth inhibition was determined by T/C and TGI (TGI (%) = [1-($T_{15}$-$T_0$)/($V_{15}$-$V_0$)] × 100);
[c]p value was calculated according to the tumor volume.

Figure 2:
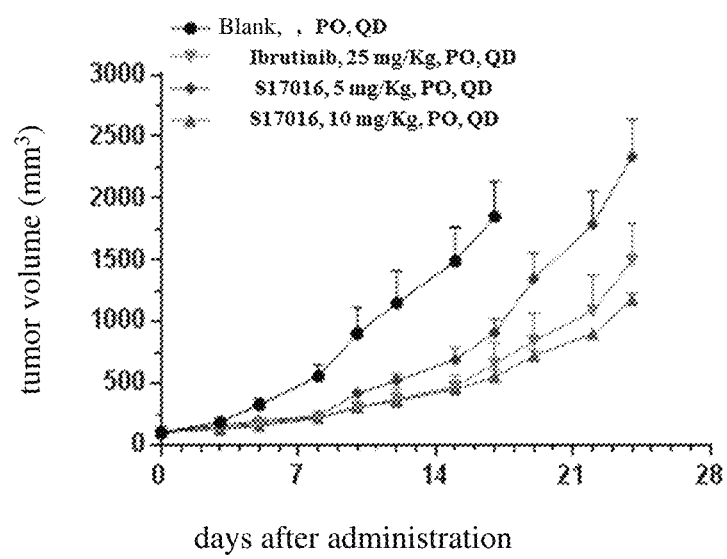
FIG. 2: Schematic diagram of experimental results of TMD-8 xenograft tumor model.

The in vivo efficacy of compound S17016 in human lymphoma TMD8 xenograft model was shown in Table 6 and FIG. 2. The tumor volume of the mice in the solvent control group reached 1852 mm³ on the 17th day after administration, Ibrutinib 25 mg/kg had significant anti-tumor effect compared with vehicle control group (T/C=35.68%, TGI=68.18%, p<0.001), the tumor volume was 661 mm³. The tumor volumes of compound S17016 in 5 mg/kg and 10 mg/kg groups were 912 mm³ and 553 mm³, respectively. Compared with vehicle control group, it had a significant anti-tumor effect (T/C was 49.27% and 29.85%, TGI was 53.78% and 74.35%, p=0.003 and <0.001).

TABLE 6

Evaluation of antitumor efficacy of S17016 on TMD8 xenograft tumor model (calculated based on tumor volume on the 17th day after administration)

| Group | Tumor volume (mm³)[a] (Day 15) | T/C[b] (%) | TGI[b] (%) | p value[c] |
|---|---|---|---|---|
| Blank control | 1852 ± 280 | — | — | — |
| Ibrutinib (25 mg/kg) | 661 ± 168 | 35.68 | 68.18 | <0.001 |
| S17016 (5 mg/kg) | 912 ± 114 | 49.27 | 53.78 | 0.003 |
| S17016 (10 mg/kg) | 553 ± 56 | 29.85 | 74.35 | <0.001 |

Note:
[a]Mean ± SEM;
[b]Tumor growth inhibition was determined by T/C and TGI (TGI (%) = [1-($T_{17}$-$T_0$)/($V_{17}$-$V_0$)] × 100);
[c]p value was calculated according to the tumor volume.

The results showed that in two BTK-sensitive mouse transplanted tumor models, compound S17016 had significant tumor growth inhibitory activity, which was obviously superior to Ibrutinib, the first generation BTK inhibitor currently on the market.

In addition, using compound S18s, the above experiment in human lymphoma TMD8 xenograft tumor model was repeated, and the T/C (%) results were listed in the following table. In the following table, T/C (%) results for compound S17016 were also listed for comparison.

| | T/C (%) | |
|---|---|---|
| Days | S18s (15 mg/kg) | S17016 (10 mg/kg) |
| 0 | 100 | 100 |
| 5 | — | 48.31 |
| 6 | 53.51 | — |
| 8 | 47.28 | 39.22 |
| 10 | — | 34.25 |
| 11 | 37.73 | — |
| 12 | — | 30.90 |

-continued

| Days | S18s (15 mg/kg) | S17016 (10 mg/kg) |
|---|---|---|
| 13 | 34.97 | — |
| 15 | — | 30.56 |
| 17 | — | 29.85 |

It can be seen from the above data that at a lower dose (10 mg/kg), compound S17016 showed better tumor growth inhibition effect than compound S18s (15 mg/kg).

Experimental Example 4: Evaluation of Metabolic Properties in Rats

Fourteen SD rats, male, weighing 200-220 g, were randomly divided into 4 groups (4/3 rats in each group) and given the tested compounds by intragastric administration and intravenous administration respectively. The specific arrangement was shown in Table 7 below:

TABLE 7

| Group | Number of animals | Compound | Route of administration | Dosage (mg/kg) |
|---|---|---|---|---|
| 1 | 4 | S17016 | Intragastric (po) | 3 |
| 2 | 3 | S17016 | intravenous (iv) | 1 |

0.5% sodium carboxymethyl cellulose (CMC-Na) containing 1% Tween 80 was formulated for intragastric administration, and 5% DMSO/5% Tween 80/90% normal saline was formulated for intravenous administration.

Fasting for 12 hours and drinking water freely before the test. Eat uniformly 2 hours after administration.
Blood Collection Time Point and Sample Treatment:
   Intragastric administration: 0.25, 0.5, 1.0, 2.0, 4.0, 6.0, 8.0 and 24 hours after administration;
   Intravenous administration: 5 minutes, 0.25, 0.5, 1.0, 2.0, 4.0, 6.0, 8.0 and 24 hours after administration;
At the above set time point, 0.3 ml of venous blood was taken through the posterior venous plexus of the rat eyeball, placed in a heparinized test tube, centrifuged at 11000 rpm for 5 minutes, and the plasma was separated, frozen in the fridge at −20° C.
Sample Testing and Data Analysis
   The concentration of S17016 in rat plasma was determined by LC/MS/MS.
   The non-compartment model of WinNonlin 5.3 software (Pharsight Company, USA) was used to calculate the pharmacokinetic parameters after administration.
   Peak concentration $C_{Max}$ and peak time $T_{Max}$ were the measured value;
   Area under drug time curve $AUC_{0-t}$ value: Calculated by trapezoidal method;

$$AUC_{0-\infty}=AUC_{0-t}+C_t/k_e,$$

$C_t$ is the blood drug concentration at the last measurable time point,
   $k_e$ is the eliminate rate constant;
   Eliminate half-life $t_{1/2}=0.693/k_e$;
   Average residence time MRT=AUMC/AUC.
   Clearance rate CL=D/$AUC_{0-\infty}$; Steady-state distribution volume Vss=CL×MRT
   Absolute bioavailability F=($AUC_{Intragastric}$×$D_{Intravenous}$)/($AUC_{Intravenous}$×$D_{Intragastric}$)×100%

The test results were shown in Table 8 below.

TABLE 8

| | iv (1 mg/kg) | | | po (3 mg/kg) | | | |
|---|---|---|---|---|---|---|---|
| Compound | CL (mL/min/kg) | $V_{SS}$ (mL/kg) | $T_{1/2}$ (h) | $C_{max}$ (ng/mL) | $T_{max}$ (h) | AUC (ng·h/ml) | F (%) |
| Ibrutinib | 61.2 | 1838 | 0.42 | 39 | 0.25 | 57 | 4.0 |
| S17016 | 3.33 | 221 | 1.26 | 2700 | 0.25 | 3856 | 24.8 |

The above results indicated that the clearance rate in vivo of S17016 in rats was significantly lower than that of Ibrutinib (20 times), and the drug exposure in plasma was as high as 70 times of that of Ibrutinib, that is, the oral absorption of S17016 was better at the same dose, and S17016 had better oral bioavailability.

Experimental Example 5: Metabolic Stability Test

Liver microsomes were incubated in a 96-well plate, and the volume of each incubated system was 450 μL with a medium of 0.1 M Tris buffer (pH 7.4), including liver microsomes with a final concentration of 0.33 mg/ml, 0.1 μM of tested drugs and 5.0 mM $MgCl_2$, 0.01% DMSO, 0.005% BSA and 1.0 mM NADPH. Incubated at 37° C. for 10 min, NADPH was added to initiate the reaction, and 50 μL was taken out and added with the same volume of methanol to terminate the reaction after 0, 7, 17, 30 and 60 min, respectively.
Sample Testing and Data Analysis
   S17016 in incubated samples was determined by LC/MS/MS with electrospray ionization (ESI) as the ion source and multi-reaction monitoring (MRM) as the scanning mode.
   The experimental results of metabolic stability in vitro of S17016 in different liver microsomes (HLM: human liver microsomes; RLM: rat liver microsomes; MLM: mouse liver microsomes) were shown in Table 9 and FIG. 3 below.

TABLE 9

| | Time | Absolute value of peak area | | |
|---|---|---|---|---|
| | (minutes) | HLM | RLM | MLM |
| M0: parent compound | 7.43 | 20285 (97.45%) | 12675 (84.07%) | 19033 (97.82%) |
| M1: Amide hydrolysate | 4.86 | — | — | 94.3 |
| M2: Monoxide product | 6.85-7.04 | 531 | 2294 | 329.2 |
| M3: Dioxide product | 6.32 | — | 107 | — |

The results showed that S17016 was mainly prototype drug in human, mouse and rat liver microsomes, and there was no large proportion of metabolites. It effectively overcame the hydroxylation of benzene ring at the end of diphenyl ether structure in S1, S10, S18s and S19s, and had good metabolic stability.

Therefore, compound S17016 is a novel, oral, highly selective and highly active BTK inhibitor. Its activity in vivo and in vitro is obviously better than that of BTK inhibitors listed abroad at present. Under the same dose, its tumor growth inhibitory activity is significantly better than that of Ibrutinib, a positive control drug, and it is of great development value.

The above embodiments are intended by way of auxiliary illustration only and are not intended to limit the embodiments that are the object of the application or the application or use of these embodiments. In this context, the term "illustrative" means "as an instance, example, or illustration". Any illustrative embodiment herein is not necessarily construed as preferred or more advantageous over other embodiments.

Further, although at least one illustrative embodiment or comparative example has been proposed in the foregoing embodiments, it should be understood that numerous variations may be present in the present invention. It should also be understood that the embodiments described herein are not intended to limit in any way the scope, use or configuration of the requested application object. On the contrary, the foregoing embodiments will provide a convenient guide for those with ordinary knowledge in the art to implement one or more of the described embodiments. Furthermore, various changes can be made to the function and arrangement of elements without departing from the scope defined by the patent application, which includes known equivalents and all foreseeable equivalents at the time of filing of this patent application.

The invention claimed is:

1. A pyrimido[5,4-b]pyrrolizin compound represented by formula I, pharmaceutically acceptable salts, enantiomers, diastereomers, optical isomers, racemates, deuterated derivatives thereof:

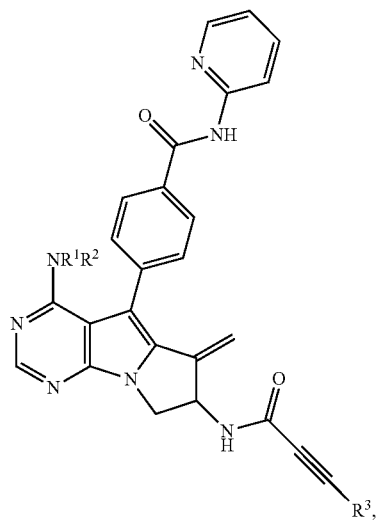

I wherein $R^1$ and $R^2$ are each independently H or $C_1$-$C_{10}$ alkyl;

$R^3$ is H or $C_1$-$C_{10}$ alkyl.

2. The pyrimido[5,4-b]pyrrolizin compound, pharmaceutically acceptable salts, enantiomers, diastereomers, optical isomers, racemates, deuterated derivatives thereof of claim 1, wherein the compound of formula I is

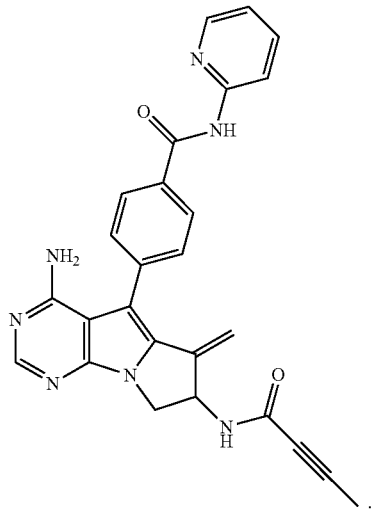 [SMILES: C=C1c2c(-c3ccc(C(=O)Nc4ccccn4)cc3)c3c(N)ncnc3n2CC1NC(=O)C#CC]

3. A method for preparing the pyrimido[5,4-b]pyrrolizin compound of claim 1, comprising the steps of:

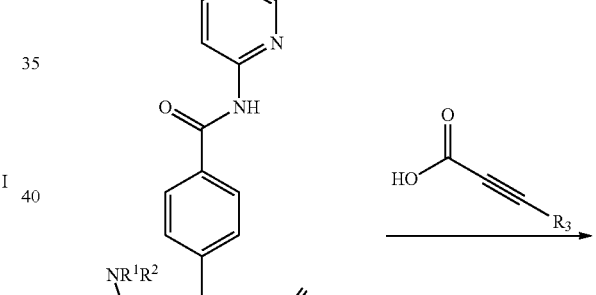

A8

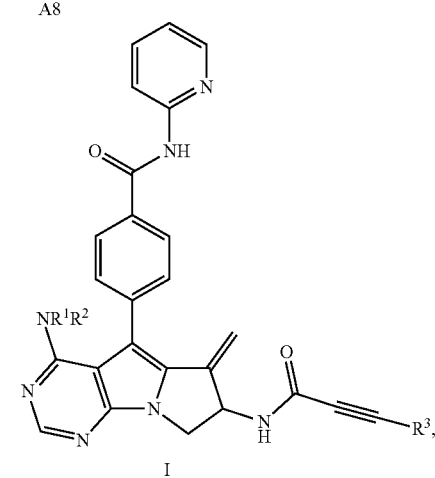

I

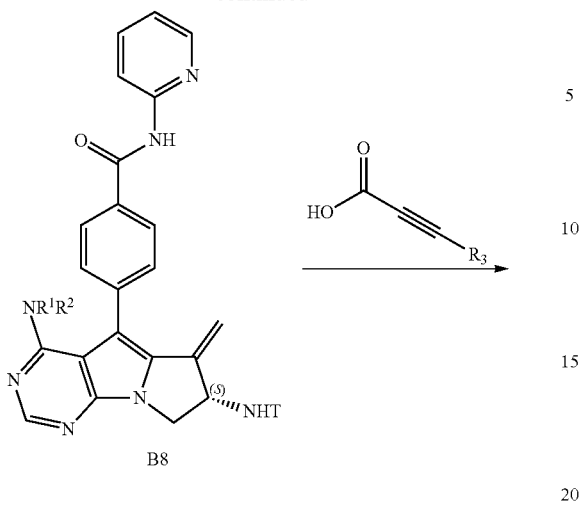

B8

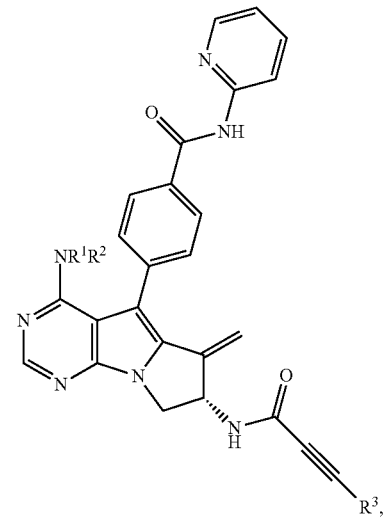

I-1 wherein R¹, R², R³ are as defined in claim 1, removing the protective group T from reactant A8 or B8, and then reacting with

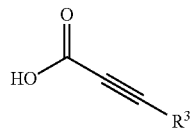

to obtain the compound of the formula I, wherein the protective group T comprises tert-butoxycarbonyl, benzyloxycarbonyl, fluorenylmethyloxycarbonyl, allyloxycarbonyl, trimethylsilylethoxycarbonyl, methoxycarbonyl, ethoxycarbonyl, phthalimido, p-toluenesulfonyl, trifluoroacetyl, triphenylmethyl, 2,4-dimethoxybenzyl, p-methoxybenzyl, benzyl and the like.

4. A pharmaceutical composition comprising a therapeutically effective amount of the pyrimido[5,4-b]pyrrolizin compound, pharmaceutically acceptable salts, enantiomers, diastereomers, optical isomers, racemates, deuterated derivatives thereof of claim 1 and one or more pharmaceutically acceptable carriers.

5. The pharmaceutical composition of claim 4, wherein the pharmaceutical composition comprises 65% to 99% by total weight ratio of the pyrimido[5,4-b]pyrrolizin compound, pharmaceutically acceptable salts, enantiomers, diastereomers, optical isomers, racemates, deuterated derivatives thereof as active ingredients.

6. The pyrimido[5,4-b]pyrrolizin compound, pharmaceutically acceptable salts, enantiomers, diastereomers, optical isomers, racemates, deuterated derivatives thereof of claim 1, wherein the compound of formula I is a compound of formula I-1, wherein R¹, R² and R³ are as defined in claim 1.

7. The pyrimido[5,4-b]pyrrolizin compound, pharmaceutically acceptable salts, enantiomers, diastereomers, optical isomers, racemates, deuterated derivatives thereof of claim 1, wherein R¹ and R² are each independently H or $C_1$-$C_6$ alkyl.

8. The pyrimido[5,4-b]pyrrolizin compound, pharmaceutically acceptable salts, enantiomers, diastereomers, optical isomers, racemates, deuterated derivatives thereof of claim 1, wherein R¹ and R² are each independently H or $C_1$-$C_3$ alkyl.

9. The pyrimido[5,4-b]pyrrolizin compound, pharmaceutically acceptable salts, enantiomers, diastereomers, optical isomers, racemates, deuterated derivatives thereof of claim 1, wherein R³ is H or $C_1$-$C_6$ alkyl.

10. The pyrimido[5,4-b]pyrrolizin compound, pharmaceutically acceptable salts, enantiomers, diastereomers, optical isomers, racemates, deuterated derivatives thereof of claim 1, wherein R³ is H or $C_1$-$C_3$ alkyl.

11. The pyrimido[5,4-b]pyrrolizin compound, pharmaceutically acceptable salts, enantiomers, diastereomers, optical isomers, racemates, deuterated derivatives thereof of claim 1, wherein the compound of formula I is

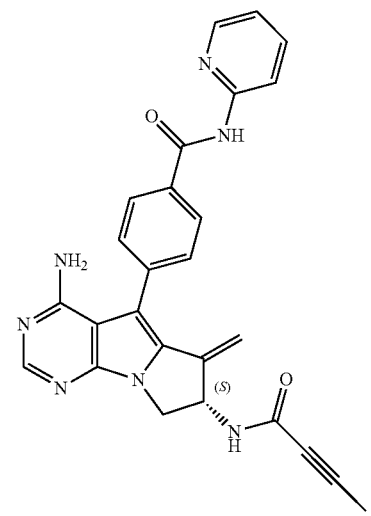

12. The method of claim 3, wherein the protective group T comprises tert-butoxycarbonyl, benzyloxycarbonyl, fluorenylmethyloxycarbonyl, allyloxycarbonyl, trimethylsilylethoxycarbonyl, methoxycarbonyl, ethoxycarbonyl.

13. The method of claim 3, wherein the protective group T comprises tert-butoxycarbonyl.

14. The method of claim 3, wherein the compound A8 is compound B8, the compound of formula I is the compound of formula I-1;

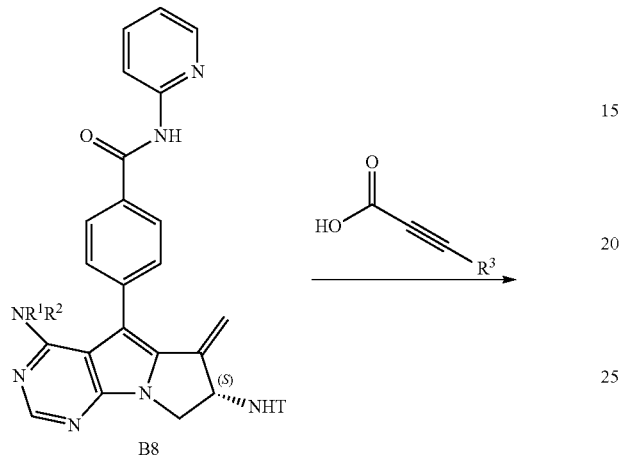

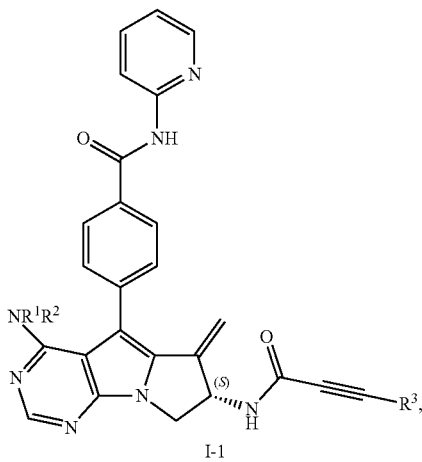

wherein $R_1$, $R_2$, $R_3$ are as defined in claim 1.

* * * * *